United States Patent [19]

Brandley et al.

[11] Patent Number: 5,094,731
[45] Date of Patent: * Mar. 10, 1992

[54] ELECTRO-BLOTTING OF ELECTROPHORETICALLY RESOLVED FLUORESCENT-LABELED SACCHARIDES AND DETECTION OF ACTIVE STRUCTURES WITH PROTEIN PROBES

[75] Inventors: Brian K. Brandley; Paul G. James, both of Alameda; Michael Tiemeyer, Oakland, all of Calif.

[73] Assignee: Glycomed, Inc., Alameda, Calif.

[*] Notice: The portion of the term of this patent subsequent to Dec. 4, 2007 has been disclaimed.

[21] Appl. No.: 589,431

[22] Filed: Sep. 27, 1990

Related U.S. Application Data

[63] Continuation-in-part of Ser. No. 481,367, Feb. 16, 1990, Pat. No. 5,019,231.

[51] Int. Cl.$^5$ ............................................. G01N 27/26
[52] U.S. Cl. ............................. 204/182.1; 204/182.8; 204/299 R; 536/127
[58] Field of Search ............... 204/180.1, 182.1, 182.8, 204/299 R; 536/127

[56] References Cited

U.S. PATENT DOCUMENTS

| | | | |
|---|---|---|---|
| 4,109,075 | 8/1978 | Deaton | 536/127 |
| 4,305,799 | 12/1981 | Scharz et al. | 204/182.1 |
| 4,666,581 | 5/1987 | Itoh et al. | 204/182.1 |

FOREIGN PATENT DOCUMENTS

| | | |
|---|---|---|
| WO88/10422 | 12/1988 | PCT Int'l Appl. |
| 2175690 | 12/1986 | United Kingdom |
| 2196734 | 5/1988 | United Kingdom |

Primary Examiner—John Niebling
Assistant Examiner—David G. Ryser
Attorney, Agent, or Firm—Morrison & Foerster

[57] ABSTRACT

Saccharide in mixtures are separated into groups or individual saccharides and tested for their affinity for particular proteins. The method of the invention is carried out by conjugating saccharides in a mixture with charge-generating moieties and moieties capable of fluorescing such as 4-amino-1-naphthalene sulfonic acid (ANSA) to form conjugates. The saccharide conjugates are subjected to electrophoretic resolution within gels. The resolved bands of material can be seen under ultraviolet light and are electro-blotted onto charged nylon membranes to provide a stable record of the electrophoretic separation. The blots (visible under ultraviolet light) on the nylon membranes are brought into contact with particular proteins in order to determine the binding affinity of these particular proteins to particular saccharides on the nylon membrane. The proteins are preferably bound to labels so that the binding of the proteins to the saccharides can be easily detected.

26 Claims, No Drawings

ELECTRO-BLOTTING OF ELECTROPHORETICALLY RESOLVED FLUORESCENT-LABELED SACCHARIDES AND DETECTION OF ACTIVE STRUCTURES WITH PROTEIN PROBES

CROSS-REFERENCE

This application is a continuation-in-part of our pending U.S. application Ser. No. 481,367, filed Feb. 16, 1990, now U.S. Pat. No. 5,019,231, which application is incorporated herein by reference and to which application we claim priority under 35 USC §120. Further, this application is related in part to two other co-pending U.S. applications filed concurrently with the present application on Sept. 27, 1990. One related application is entitled "Two-Dimensional Electrophoretic Separation of Carbohydrates," invented by Brian K. Brandley and Robert J. Stack; the other application is entitled "Fluorescent Tag for Sugar Electrophoresis," invented by Brian K. Brandley, Michael Tiemeyer and Robert J. Stack, all of whom are co-inventors working in the same research organization as the present inventors with an obligation to assign the invention to the same entity. The above-referenced applications are each incorporated herein by reference in their entireties.

FIELD OF THE INVENTION

This invention relates generally to separation techniques such as electrophoresis and electro-blotting which allow for the separation of particular materials and then testing of those materials for activity utilizing labeled probes. More particularly, the invention relates to utilizing electrophoresis followed by electro-blotting in order to separate mixtures of saccharides containing very small amounts of fluorescent labeled saccharides and then determining the activity of such saccharides by using labeled protein probes.

BACKGROUND OF THE INVENTION

Electrophoresis is a well known technique for the separation of a charged species by utilizing their differences in rate of migration under the influence of an electrical field The procedure has proved invaluable for the resolution and isolation of complex biological substances such as enzymes, serums, carbohydrates, proteins, DNA and RNA. Most analytical electrophoresis methods are based on zone-electrophoresis in which a thin zone of a sample material is applied to the electrophoretic medium. The electrophoretic migration of the sample components results in the formation of fractional zones. These zones can be examined and studied by applications of standard electrophoretic practice such as fixing, staining and washing to remove buffers. Desirably, the electrophoretic media is a thin gel film coated on a suitable support, commonly glass or plastic. Such an arrangement permits the electrophoretic separation to be achieved in a minimum of time with a maximum degree of resolution.

Various hydrophilic colloids, for example, starch, agarose and cellulose derivatives have been used in forming electrophoretic gel films, but polyacrylamide is preferred. One reason for preferring polyacrylamide is that gels can be prepared from it having a wide range of pore size. This is accomplished primarily by varying the ratio of acrylamide polymer to the N, N', methylenebisacrylamide cross-linking reagent.

The resulting polyacrylamide gels provide high resolution electrophoretic separation of important biopolymers, for example, proteins and nucleic acids. In addition, the absence of ionized groups in polyacrylamide gels render such gels suitable as an anticonvection medium for isoelectric focusing Once the electrophoretic techniques have been applied in order to separate the materials in the gel, it is necessary to transfer the separated materials from the gel to a support where they can be tested A number of procedures are available for transferring the electrophoretically resolved materials from the gel. One such procedure involves electro-blotting. This type of transfer procedure involves transferring the resolved bands within the gel to a support matrix such as a nitrocellulose sheet. The transfer is carried out by the application of an electric field and therefore is distinguishable from a more conventional alternative which involves the capillary transfer of such materials usually used in techniques such as southern and northern blotting.

SUMMARY OF THE INVENTION

In accordance with the present invention mixtures of saccharides are resolved into groups and tested for their affinity to particular proteins The process is carried out by conjugating the saccharides in the mixture to a charged molecule which is capable of fluorescing and then subjecting the charged conjugates to electrophoretic techniques in order to separate the different saccharides or groups of saccharides from each other. After carrying out electrophoretic resolution, the resolved bands within the gel are electro-blotted onto a membrane which is preferably a charged nylon membrane. The nylon membrane provides a stable record of the electrophoretic separation in the gel. The membrane having the bands of saccharides thereon is then subjected to testing techniques with various labeled protein compounds. If the protein binds to the saccharide material, the binding can be detected by the label and the saccharide is determined as being one of particular interest due to its binding affinity to the protein and can be further studied.

A primary object of the present invention is to provide a method for separating mixtures of saccharides into closely related groups of saccharides and determining which groups of specific saccharides have particular binding affinities to particular proteins.

An advantage of the present invention is that large numbers of different saccharides each present in small amounts in mixtures can be readily separated into bands (and the bands can be seen under ultraviolet light due to their fluorescent character) and readily tested for their affinity to large numbers of proteins.

A feature of the present invention is that it involves a unique combination of separation and probing techniques which can be readily and efficiently carried out to obtain large amounts of information with respect to particular saccharides.

These and other objects, advantages and features of the present invention will become apparent to those persons skilled in the art upon reading the details of the structure, synthesis and usage as more fully set forth below, reference being made to the accompanying general structural formulae forming a part hereof.

DETAILED DESCRIPTION OF PREFERRED EMBODIMENTS

Before the present method for separating and testing saccharides is described, it is to be understood that this invention is not limited to the particular saccharides, proteins, charge-generating fluorescent moieties or process steps described as such compounds and steps may, of course, vary. It is also to be understood that the terminology used herein is for the purpose of describing particular embodiments only and is not intending to be limiting since the scope of the present invention will be limited only by the appended claims.

It must be noted that as used in the specification and the appended claims, the singular forms "a", "an" and "the" include plural referents unless the context clearly dictates otherwise. Thus, for example, reference to "a protein" includes mixtures of proteins, reference to "an oligosaccharide" or a saccharide includes reference to mixtures of oligosaccharides or saccharides, and reference to "the electrophoretic processing step" includes a variety of similar steps of the type described herein.

The first step of the present invention involves binding the saccharide molecules to be tested to charged moieties which are capable of fluorescing. The charged moiety must be attached in order to allow the mixtures of saccharides to be separated from each other by electrophoretic techniques which apply a charge differential in a field and thus require that the materials being separated have electrical charges thereon. In connection with the present invention, the carbohydrates (preferably saccharides) are conjugated with one or more suitable moieties such as 4-amino-1-naphthalene sulfonic acid (hereinafter ANSA).

The preferred conjugates of the invention are bi-functional conjugates formed by binding carbohydrates (in a mixture to be separated) to a bi-function moiety. Although such moieties are generally useful if they (a) provide a charge and (b) are capable of fluorescing, preferred moieties are characterized by having (1) a primary amine (which can react with and bind to a saccharide), (2) one or more charged groups (which allow movement in a charged field), (3) a fluorescent moiety (allowing bands to be visualized under U.V. light), and (4) a relatively small molecular weight, e.g., less than 500, preferably 200-300 (so as to not interfere with the electrophoretic separations.

The present invention can be used in order to separate a wide range of carbohydrates. However, the particular abilities of the separation techniques of the invention are more clearly demonstrated when the invention is used to separate saccharides and particularly smaller saccharides such and mono-, di-, and trisaccharides. Throughout this disclosure, the terms "carbohydrate" and "saccharide" are at times used interchangeably in that the particular structure of the compounds being separated is not part of the present invention. However, the more closely related the compounds being separated are to each other, the more useful the present invention becomes.

As indicated above, the first step of the present invention is to conjugate the carbohydrate to a moiety which provides a charge and is capable of fluorescing. That moiety is preferably a single moiety which is capable of generating a charge upon ionizing and capable of fluorescing when subjected to ultraviolet light. However, the carbohydrate may be bound to two separate moieties wherein one of the moieties is capable of generating a charge upon ionization and the other moiety is capable of fluorescing upon being subjected to ultraviolet light. When two separate moieties are used, the charge generating moiety need not be fluorescent and the fluorescent moiety need not generate any charge. If two separate moieties are used to impart the two separate characteristics to the carbohydrate, then the two separate moieties may be bound directly and individually to the carbohydrate or may be bound to each other and thereafter either of the moieties bound directly to the carbohydrate. Naphthalene and fluorescein are examples of moieties which are capable of fluorescing when subjected to ultraviolet light and preferably include an amine to allow binding to the carbohydrate. Various sulfonates and carbonates are examples of moieties capable of providing a charge to the carbohydrate upon ionization.

Examples of bi-functional moieties capable of providing a charge upon ionization and of fluorescing upon being subjected to ultraviolet light include:

1-amino-4-(2-hydroxyethyl)piperazine;
2-amine-9-hydroxyfluorene;
2-amino-6-hydroxy-8-mercaptopurine;
4-amino-6-hydroxy-2-mercaptopyrimidine monohydrate;
2-amino-4-hydroxy-6-methylpyrimidine;
4-amino-3-hydroxy-1-naphthalenesulfonic acid;
4-amino-6-hydroxy-1-naphthalenesulfonic acid;
6-amino-4-hydroxy-2-naphthalenesulfonic acid monohydrate;
7-amino-4-hydroxy-2-naphthalenesulfonic acid monohydrate;
3-amino-5-hydroxypyrazole;
4-amino-6-hydroxypyrazolo[3,4-d]pyrimidine;
4-amino-1-naphthalenecarbonitrila;
3-amino-2,7-naphthalenedisulfonic acid, monosodium salt;
7-amino-1,3-naphthalenedisulfonic acid, monopotassium salt;
2-amino-1-naphthalenesulfonic acid;
4-amino-1-naphthalenesulfonic acid;
5-amino-2-naphthalenesulfonic acid;
8-amino-2-naphthalenesulfonic acid;
4-amino-1,8-naphthalic anhydride;
4-amino-1,8-naphthalimide;
3-amino-2-naphthoic acid;
4-amino-1,2-naphthoquinone hemihydrate;
6-aminonicotinamide;
5-((2-aminoethyl)amino)naphthalene-1-sulfonic acid, sodium salt; and
N-(2-aminoethyl)-4-amino-3,6-disulfo-I,8-naphthalimide, dipotassium salt.

Any salts of the above-listed acids or acids of the above-listed salts can also be used.

In connection with a preferred embodiment of the invention, one of more ANSA moieties are bound to the carbohydrate.

The 1-amino-4-naphthalene sulfonic acid (ANSA) preferably used in connection with the present invention has the following structure:

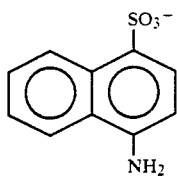

The —NH$_2$ amino group is indicated as being at the "1" position and the —SO$_3^-$ group is at the "4" position. The shared double bonds in each ring structures provides the fluorescent character to the ANSA when the ANSA is exposed to U.V. light.

Depending on the type of saccharide in the mixture being resolved, there may be additional —SO$_3^-$ groups attached to the basic ring structure. The additional —SO$_3^-$ groups provide additional charge to neutral saccharides. If two —SO$_3^-$ groups are present, the molecule is referred to as ANDA and if three are present ANTS, for example, (8-aminonaphthalene-1,3,6 trisulfonic acid).

One preferred class of charge-generating moieties capable of fluorescing can be generally described by the following general structural formula:

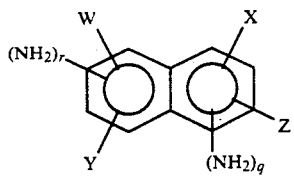

wherein each of W, X, Y and Z are independently hydrogen or an ionizable, charge-generating moiety such as —SO$_3^-$ or —CO$_2^-$, and q and r are independently 0 or 1 with the proviso that one of r or q is 1. Preferably only one of W, X, Y and Z is a charge generating moiety and it is preferably —SO$_3^-$. Further, alpha-amino naphthalenes are preferred over beta-amino naphthalenes.

After the bi-functional conjugates are formed, i.e., bound to charged and fluorescing moieties, the conjugates are subjected to standard electrophoretic techniques in order to resolve the different saccharides from each other. The electrophoretic resolution provides a gel wherein the saccharides are separated from each other in different bands along the length of the gel.

The separation techniques utilized in connection with the present invention have been found to work particularly well in connection with smaller saccharides. More specifically, the gel electrophoresis has been found to be particularly useful in separating mixtures of monosaccharides, disaccharides, and trisaccharides. Conventional procedures are generally not capable of providing sufficient resolution to separate away smaller saccharides into distinct bands. The addition of a group such as the ANSA group provides a sufficient amount of charge to allow for the separation of the smaller saccharides into distinct groups but does not apply too much charge so that the charge quality overwhelms any other quality of the saccharides and thus does not provide for resolution among different types of closely related saccharides. Further, the shared double bonds within the ring structures of the fluorescing moiety such as naphthalene or, specifically, ANSA provide for the fluorescent capability of the conjugates formed. Accordingly, when different bands of saccharides are separated away from each other, it is possible to visually view these bands simply by the application of ultraviolet light. This provides a significant advantage in that any given band can be removed and manipulated or tested as desired.

It is pointed out that some mono- and disaccharides can only be resolved into distinct groups via electrophoresis by using ANSA. The monosaccharides include glucuronic acid, iduronic acid and galacfuronic acids. The disaccharides include:
2-acetamido-2-deoxy-3-0 (BetaD-gluco-4-ene pyranosyluronic acid)-D-galactose;
2-acetamido-2-deoxy-3-0 (BetaD-gluco-4-ene pyranosyluronic acid)-4-0-sulfo-D-galactose; and
2-acetamido-2-deoxy-3-0 (BetaD-gluco-4-ene pyranosyluronic acid)-6-0-sulfo-D-galactose.

The use of such a fluorescent tag provides a number of advantages over and above the use of other types of tags. For example, a fluorescent tag is substantially safer and less expensive than the use of a radiolabel. Further, the use of a fluorescent tag is substantially less cumbersome and more efficient than the use of antibody-linked enzyme tags. These advantages are obtained concurrently with the overall advantage of providing a tag which allows for greatly improved resolution especially as used in connection with smaller saccharide compounds.

The separated bands of conjugates within the gel are then transferred to the surface of a membrane A number of different types of membrane surfaces can be utilized in connection with the invention. However, nylon is preferable as is a surface of polyisobulylene methylmethacrylate. The transfer of the saccharide conjugates from the gel to the surface of the substrate is carried out by utilizing electro-blotting techniques. The electro-blotting is carried out for a sufficient period of time to allow substantial amounts of the conjugates within the gel to transfer to and bind to the surface of the substrate thus providing a permanent record of the separated bands of conjugates on the surface of the membrane.

The electro-blotting procedures which can be used in connection with the present invention are procedures which are generally known to those skilled in the art. In general, a gel having the separated conjugates thereon is placed in contact with a membrane surface. The membrane surface which is preferably a charged nylon surface is preferably first wetted with a buffer in which the electro-blotting procedure will be carried out. What is arbitrarily chosen as the cathode side of the gel (i.e., ultimately towards the negative electrode when positioned in the electro-blotting tank) is placed in contact with the surface of the nylon substrate after the substrate has been moistened with the electro-blotting buffer. Any air bubbles between the gel and the nylon membrane should be removed by gently pushing the nylon substrate against the gel using powder-free gloved fingers. A piece of nitrocellulose can be placed on the opposite side of the gel and all of the air bubbles should be removed between the gel and the nitrocellulose. Such a construct is then placed in the electro-blotting tank which contains a buffer solution and has an anode and a cathode therein. The power supply is then turned on and the power supply will draw the electrically charged saccharide conjugates out of the gel and onto the charged surface of the nylon substrate. The transfer time is dependent somewhat on the thickness of the gel and the size of the conjugates being transferred to the nylon substrate. The transfer can be monitored by viewing the transfer under U.V. light to insure complete transfer of all of the materials to the nylon substrate surface. Overnight transfer is reliable and convenient.

One of the surprising discoveries of the present invention is that the specific bands of conjugates in the gel are even more clearly resolved and distinguishable from each other when the transfer is made to the nylon substrate surface. While not wishing to be bound to any particularly theory, it is believed that greater resolution is obtained on the nylon surface because of the diffusion of light in the gel when the conjugates are exposed to U.V. light. Regardless of the reason, it has been found that distinct, separate bands of conjugates are formed on the nylon substrate surface.

It is possible to increase the ability of the methods of the invention to detect small amounts of carbohydrates by binding moieties which fluoresce but do not impart additional charge, e.g., naphthalene. The inclusion of large additional charge would overwhelm the separation procedure to the extent that other characteristics of the saccharide would not be borne out when separating closely related smaller saccharides.

After the conjugates on the membrane surface have been secured to the surface, the specific saccharides within each of the visually detectable groups can then be tested for their affinity to other molecules. This testing is generally done by first forming conjugates of molecules to be tested by binding such molecules to a label. For example, protein molecules are bound to a radiolabel. The conjugates of radiolabeled proteins are then brought into contact with the saccharide conjugates on the surface of the membrane. If the proteins have an affinity to the saccharides on the membrane, they will bind to the saccharides, thus forming double conjugates, i.e., the saccharide conjugates bind to the protein/label conjugates.

After the protein/label conjugates have been allowed to remain in contact with the membrane surface for a sufficient period of time to allow for complete binding, the membranes are washed thoroughly in order to remove any unbound protein. After the unbound proteins are removed, the bound proteins, if any, are detected by utilizing the label attached to the proteins by procedures such as radiography.

The separation methodology of the present invention can be utilized in order to test a variety of different types of compounds for their affinity to the saccharides on the nylon substrate. For example, the invention can be utilized in order to test the affinity of certain lectins for their affinity to the saccharides. Particular types of antireceptor proteins known to be positioned on viruses and to be attachable to certain saccharides on cell surfaces can be tested. Further, the affinity of certain growth factor proteins can be tested. It is believed that the attachment of certain saccharides to growth factor proteins can effect the activity of the growth factor protein in vivo.

The molecules to be tested, such as the protein molecules to be tested for their affinity to saccharides, must, of course, be bound to a label which is later detectable. A variety of different types of labels known to those skilled in the art can, of course, be used. For example, it is possible to utilize radiolabels which are later detected by the use of autoradiography. It is also possible to attach the protein molecules to an antibody which itself is bound to an enzyme such as horseradish peroxidase which can be detected by the addition of reagents which cause a color change. Procedures for attaching the labels to the proteins or other molecules to be assayed are well known to those skilled in the art.

The following examples are provided so as to give those of ordinary skill in the art a complete disclosure and description of how to carry out the processes of the invention and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, temperature is in degrees centigrade, and pressure is at or near atmospheric.

EXAMPLE 1

Charged saccharides in the form of heparin fragments from partial nitrous acid digests are reacted with ANSA to form conjugates. The reaction is carried out in 10 to 100 mM sodium acetate buffer (pH 5.0). The heparin fragments are present in an amount of 0.01-1 $\mu$mol/ml and are reacted with ANSA and sodium cyanoborohydride in a ten fold molar excess with respect to the reducing end sugar of the heparin fragment. The derivatized heparin fragments are then subjected to electrophoretic resolution in 40% acrylamide/5% bis gels, with a Tris/glycine buffer system (25 mM Tris, 195 mM glycine, pH 8.3). The electrophoretic gel is to be run at 300 volts for approximately 90 minutes. The gels are to be immediately electro-blotted using a Biorad apparatus onto a Zetaprobe membrane (of the type commercially sold by Biorad). The electro-blotting is carried out utilizing standard techniques and 100 volts for one hour with the same Tris/glycine buffer system. After completing the electro-blotting, the Zetaprobe membranes are removed and air dried.

The drying membranes have the separated heparin fragments bound thereon. These membranes with the heparin bound thereon are stable on PBS at least overnight. Accordingly, such blots can be blocked with 2% PVP40 (Sigma) in PBS for 1 hour at room temperature and then probed with proteins (radioiodinated bFGF) overnight at 4° C., in PBS plus 2% PVP40. After allowing any binding to take place, the membrane are washed with the same buffer three times, and then dried. Bound protein can be detected by autoradiography. The ANSA provides a fluorescent label on the heparin fragment will allow for the direct visualization of the blot and comparison of it with the autorad, i.e., the membrane having the radiolabeled proteins bound thereto.

EXAMPLE 2

Neutral saccharides in the form of tetrose derived from asialo-GM1 were charged by reacting them with ANSA to form conjugates. The reaction conditions were 10-100 mM sodium acetate buffer (pH 5.0), asialo-GM1 at 0.01-1 $\mu$M/ml, ANSA and sodium cyanoborohydride in tenfold molar excess to the reducing end of the sugar. Derivatized saccharides were resolved in 40% acrylamide/5% bis gels with a Tris/glycine buffer system (25 mM Tris, 195 mM glycine pH 8.3) run at 300 volts for approximately 90 minutes. The gels were immediately electro-blotted using a Biorad apparatus onto Zetaprobe membranes (manufactured by Biorad) by standard techniques (100 volts, 1 hour) with the same Tris/glycine buffer system.

It was found that the ANSA tag did not apparently impart sufficient charge to keep these neutral saccharides stably associated with the membrane in buffer solutions. Accordingly, the membranes were first wetted with hexanes, then soaked in 0.1 percent polyisobutylene methylmethacrylate in hexanes for 45-60 seconds and were dried. These membranes were probed in 50 mM buffers.

The instant invention is shown and described herein in what is considered to be the most practical, and preferred embodiments. It is recognized, however, that departures may be made therefrom which are in the scope of the invention and that obvious modifications will occur to one skilled in the art upon reading this disclosure.

What is claimed is:

1. A method of separating and analyzing saccharides within a mixture of saccharides, comprising the steps of:
   reacting the saccharides in the mixture with charge-generating moieties and moieties capable of fluorescing in order to form saccharide conjugates;
   subjecting the saccharide conjugates to electrophoretic separation in a gel;
   electro-blotting the separated saccharides in the gel to the surface of a support membrane; and
   contacting labeled probes with the membrane and determining binding affinity of the probes to saccharides on the membrane.

2. The method as claimed in claim 1, wherein the charge-generating moieties and moieties capable of fluorescing are the same moieties which are charge-generating moieties capable of fluorescing.

3. The method as claimed in claim 2, wherein the charge-generating moieties capable of fluorescing are selected from the group consisting of:
1-amino-4-(2-hydroxyethyl)piperazine;
2-amine-9-hydroxyfluorene;
2-amino-6-hydroxy-8-mercaptopurine;
4-amino-6-hydroxy-2-mercaptopyrimidine monohydrate;
2-amino-4-hydroxy-6-methylpyrimidine;
4-amino-3-hydroxy-1-naphthalenesulfonic acid;
4-amino-6-hydroxy-1-naphthalenesulfonic acid;
6-amino-4-hydroxy-2-naphthalenesulfonic acid monohydrate;
7-amino-4-hydroxy-2-naphthalenesulfonic acid monohydrate;
3-amino-5-hydroxypyrazole;
4-amino-6-hydroxypyrazolo[3,4-d]pyrimidine;
4-amino-1-naphthalenecarbonitrila;
3-amino-2,7-naphthalenedisulfonic acid, monosodium salt;
7-amino-1,3-naphthalenedisulfonic acid, monopotassium salt;
2-amino-1-naphthalenesulfonic acid;
4-amino-1-naphthalenesulfonic acid;
5-amino-2-naphthalenesulfonic acid;
8-amino-2-naphthalenesulfonic acid;
4-amino-1,8-naphthalic anhydride;
4-amino-1,8-naphthalimide;
3-amino-2-naphthoic acid;
4-amino-1,2-naphthoquinone hemihydrate;
6-aminonicotinamide;
5-((2-aminoethyl)amino)naphthalene-1-sulfonic acid, sodium salt; and
N-(2-aminoethyl)-4-amino-3,6-disulfo-1,8-naphthalene, dipotassium salt
and any salts of the acids and acids of the salts.

4. The method as claimed in claim 2, wherein the charge-generating moieties capable of fluorescing have a molecular weight of less than 500 and include an amino group.

5. The method as claimed in claim 1, wherein the charge-generating moieties are selected from the group consisting of sulfonates and carbonates.

6. The method as claimed in claim 1, wherein the moieties capable of fluorescing are selected from the group consisting of: naphthalene, fluorescein, aminonaphthalene and amino fluorescein.

7. The method as claimed in claim 1, wherein the mixture of saccharides is a mixture of heparin fragments obtained from partial nitrous acid digests.

8. The method as claimed in claim 1, wherein the saccharide mixture includes tetrose derived from asialo-GM1.

9. The method as claimed in claim 1, wherein the mixture of saccharides includes neutral oligosaccharides.

10. The method as claimed in claim 9, further comprising:
    coating the surface of the membrane having the saccharides electro-blotted thereon with polyisobutylene methylmethacrylate.

11. The method as claimed in claim 1, wherein the mixture of saccharides includes saccharides selected from the group consisting of mono-, di- and trisaccharides.

12. The method as claimed in claim 1, wherein the labeled probe is a labeled protein probe.

13. A method of resolving a mixture of saccharides into distinct bands of saccharides which are closely related or identical, comprising the steps of:
    reacting the mixture of saccharides with charge-generating moieties and moieties capable of fluorescing to form saccharide conjugates;
    subjecting the conjugates to gel electrophoresis separation by the application of an electrical field for a sufficient period of time to form the separate bands in the electrophoresis gel;
    transferring the separate bands of saccharides in the electrophoresis gel onto a membrane surface; and
    exposing the membrane surface to ultraviolet light to determine the bands of saccharides.

14. A method of separating a mixture of carbohydrate, comprising the steps of:
    reacting the carbohydrate mixture with charge-generating moieties capable of fluorescing to form conjugates;
    subjecting the conjugates to electrophoretic separation in a gel to provide separate bands of conjugates, wherein the charge-generating moieties capable of fluorescing are selected from the group consisting of monosulfonic and disulfonic acid derivatives of amino naphthalene.

15. The method as claimed in claim 14, wherein the charge-generating moieties capable of fluorescing are alpha-amino naphthalenes.

16. The method as claimed in claim 14, further comprising:
    transferring the bands out by electro-blotting the bands in the gel onto the surface of a membrane.

17. The method as claimed in claim 16, wherein the carbohydrate mixture comprises saccharides selected from the group consisting of monosaccharides, disaccharides and trisaccharides.

18. The method as claimed in claim 16, further comprising:
   contacting the membrane surface with labeled probes to determine the affinity of the probes to bind to saccharides on the membrane surface; and
   washing away any labeled probes not bound to saccharides on the surface and detecting bound probes by their label.

19. The method as claimed in claim 16, wherein the mixture of carbohydrates includes specific saccharides in an amount in the range of 1 to 10 picomoles and wherein such saccharides present in an amount of 1 to 10 picomoles are observable in distinct bands on the membrane surface when viewed under ultraviolet light.

20. The method as claimed in claim 19, wherein distinct bands of saccharides on the membrane surface includes saccharides in an amount of from 1 to 5 picomoles.

21. A membrane, the surface of which has electro-blotted thereon a plurality of distinct bands of saccharides wherein the saccharides are bound to a charge-generating moiety and a moiety capable of fluorescing.

22. The membrane as claimed in claim 21, wherein the charge-generating moiety and moiety capable of fluorescing is the same moiety which is a charge-generating moiety capable of fluorescing.

23. The membrane as claimed in claim 22, wherein the charge-generating moiety capable of fluorescing is selected from the group consisting of 4-amino-1-naphthalene sulfonic acid; and 4-amino-1-naphthalene sulfonic acid having one or two additional sulfonic acid groups attached to the naphthalene ring at the 5, 6, 7 or 8 positions of the rings.

24. The membrane as claimed in claim 23, wherein the fluorescent label is 4-amino-1-naphthalene sulfonic acid.

25. A method of separating and analyzing saccharides within a mixture of saccharides, comprising the steps of:
   reacting the saccharides in the mixture with naphthalene sulfonic acid or a derivative thereof, the reacting being carried out in order to form conjugates;
   subjecting the conjugates to electrophoretic separation in a gel;
   electro-blotting the separated saccharides in the gel onto the surface of a support membrane; and
   contacting labeled probes with the membrane and determining the binding affinity of the probes to saccharides on the membrane.

26. A bi-functional conjugate in the form of a carbohydrate having bound thereto a monosulfonic or disulfonic acid derivative of amino naphthalene or a salt thereof.

* * * * *